United States Patent [19]

Schneider

[11] Patent Number: 4,971,073
[45] Date of Patent: Nov. 20, 1990

[54] RESTRAINT JACKET

[75] Inventor: Ronald H. Schneider, Clearwater, Fla.

[73] Assignee: Ron Schneider & Associates, Inc., Clearwater, Fla.

[21] Appl. No.: 369,379

[22] Filed: Jun. 21, 1989

[51] Int. Cl.⁵ ............................................. A61F 13/00
[52] U.S. Cl. ................................... 128/874; 128/869
[58] Field of Search ............... 128/869, 870, 871, 872, 128/873, 874, 875, 876, DIG. 15

[56] References Cited

U.S. PATENT DOCUMENTS

| | | | |
|---|---|---|---|
| 4,117,840 | 10/1978 | Rasure | 128/874 |
| 4,132,230 | 1/1979 | Ladd | 128/874 |
| 4,685,454 | 8/1987 | Posey | 128/873 |
| 4,744,354 | 5/1988 | Triunfol | 128/875 |
| 4,832,053 | 5/1989 | McCarthy | 128/869 |
| 4,840,189 | 6/1989 | Wachtel | 128/869 |

Primary Examiner—Robert A. Hafer
Assistant Examiner—Lynda M. Cofsky
Attorney, Agent, or Firm—Joseph C. Mason; Ronald E. Smith

[57] ABSTRACT

A disposable restraint jacket having a pair of laterally spaced, releasably secured flaps, formed in the front of the jacket, that grant ready access to the subclavian area. The jacket is color coded as to size, is marked with indicia to indicate its front and back parts, and its neck opening prevents choking of the patient. The flaps and other confronting parts of the jacket are releasably secured by a combination of locking devices of the hook and loop type. Additional embodiments add zippers and flaps on the back of the jacket.

23 Claims, 8 Drawing Sheets

RESTRAINT JACKET

TECHNICAL FIELD

This invention relates, generally, to an improved article of clothing. More particularly, it relates to an article of clothing having utility as a restraint jacket.

BACKGROUND ART

Patients in intensive care units often require restraint. Moreover, post-operative patients are sometimes delirious and require restraint so that their surgical incisions may heal properly.

Also, patients who are seated in wheelchairs often require restraint to prevent them from sliding downwardly.

Inventors have long been interested in the art of restraint devices. For example, U.S. Pat. Nos. 4,787,101 and 4,683,594 to Feinberg both disclose shoulder seams having self-adhering strip members. Other restraint jackets or garments of interest are shown in U.S. Pats. 4,117,840 to Rasure. 3,163,311 to Lewis and 3,265,065 to Jillson. Moreover, U.S. Pat. Nos. 4,744,354 and 4,488,544 to Triunfol disclose garments of interest.

Still further U.S. patents that show Velcro ™ brand fastening means along the shoulder include Freeman, 4,570,268, Ragone 3,055,855 and Stewart 4,764,986.

Bailey patent D115,983 shows zippers along the shoulders, and Bloom 1,811,821 and Hanks 839,139 disclose seams, zippers or snaps along the front or back of garments.

Other U.S. patents showing Velcro brand fastening means, or snap fasteners, buttons, hook and eyes, and other fastener means, are shown in U.S. Pat. Nos. 3,827,107 to Moore, 4,509,214 to Shea and 3,110,903 to Burchard.

Thus, it is clear that the art is quite well developed, but there are subtle inadequacies in the known restraint jackets.

For example, restraint jackets are commonly put on backwards by health care personnel who are too preoccupied with numerous simultaneous pressing concerns to carefully study the design of a particular restraint garment before putting it on a patient. Many hastily put on restraint garments are put on backwards; due to poor design, many worn-backwards garments choke the person wearing them. Such choking is a very serious problem, especially since the average restrained patient has little control over his or her body position. The art has not produced a restraint garment that overcomes this problem.

Another important drawback of the known garments is that they must be taken off when an intravenous feeding is required in the subclavian region. Putting on and taking off restraint garments so that an IV may be attached int he subclavian region is an activity that consumes entirely too much time in modern health care institutions. Yet, the art has failed to develop restraint garments that need not be removed when a subclavian IV feed is necessary.

Moreover, although Velcro brand fastening means, zippers, and other fastening means are commonly used in various garments, such fastening means are always used as the primary closure means, and no backup closure means is provided.

DISCLOSURE OF INVENTION

The restraint jacket of the present invention has short sleeves, preferably, and is color coded, by tabs on its front and back, to indicate small, medium and large sizes so that a jacket suitable in size for a particular patient can be quickly selected by a busy health care professional.

Moreover, a first tab marketed "front" in large letters is affixed to the front of the jacket, in physical proximity to the front color coded tab, and a second tab marked "back" in large letters is affixed to the back of the jacket, in physical proximity to the back color coded tab.

The jacket has a "V" neck so that the possibility of patient choking is substantially reduced.

The back of the jacket is closed by two locking means. In other words, a primary and a backup locking means are provided. The primary locking means includes mating pairs of hook and loop fasteners; a plurality of vertically spaced Velcro strips are fixedly secured to the underside of an overlying back edge of the garment along the entire extent thereof and a second plurality of vertically spaced Velcro strips are fixedly secured in overlying relation to an underlying back edge of the garment along the entire extent thereof. The backup locking means includes a plurality of vertically spaced loop lock members that overlie and supplement the first locking means. Accordingly, the patient is unable to reach around to his or her back and uncouple both the loop lock members and the mating pairs of fasteners.

In a first embodiment, a pair of laterally spaced flaps are provided on the front of the jacket to allow intravenous feeding in the subclavian area. Each flap is releasably secured in its closed configuration by two complementary closure means, i.e., by mating Velcro hook and loop fasteners and by a Velcro loop lock means at the top of each flap. Thus, although the health care professional can easily accomplish the two step unfastening procedure to accomplish the intravenous feed, the average patient will be unable to accomplish such unfastening. When the loop locks have been fully opened, the flaps are easily folded forwardly; since each flap is independent of the other, one flap may be left closed as needed.

Each flap is bounded on its inner side by the peripheral border of the V neck and on its outer side by an edge of material that extends front he top of the V neck toward the armpit area of the jacket. The flap does not extend all the way to the armpit area. In other words, the outer edge of each flap is adjacent the lower edge of its associated sleeve member. The flap outer edge overlies the sleeve lower edge.

Another novel feature of the jacket is its provision of a pair of laterally spaced loop members in the shoulder region of the jacket, spaced to the rear of the top of the shoulders. The loop members provide attachment means for tether straps having a first end secured to a bed or wheelchair and a second end secured to its associated loop member. Tether straps and loop members are not novel, per se, but the specific positioning of the loop members of this invention are novel.

In a second embodiment, zippers are employed in lieu of the Velcro closure means for closing the flaps, and in a third embodiment, additional flaps are provided on the back of the jacket.

Other features of the jacket are essentially conventional and include an elongate transversely disposed strap that overlies the stomach region of the jacket so that the patient can be strapped into a wheelchair or a bed, and a pair of loop lock members on the opposite sides of the garment to tighten it securely against the patient's upper body.

It is therefore clear that the primary object of this invention is to advance the art of restraint garments by providing a garment that is easy to put on a patient and that need not be removed for subclavian intravenous feeding.

The invention accordingly comprises the features of construction, combination of elements and arrangement of parts that will be exemplified in the construction set forth hereinafter and the scope of the invention will be set forth in the claims.

DESCRIPTION OF THE DRAWINGS

For a fuller understanding of the nature and objects of the invention, reference should be made to the following detailed description, taken in connection with the accompanying drawings, in which:

FIG. 7 is a front elevational view of the jacket, showing how its sides are tightened to conform to the patient's body when worn;

Similar reference numerals refer to similar parts throughout the several view of the drawings.

BEST MODES FOR CARRYING OUT THE INVENTION

Figure 1:
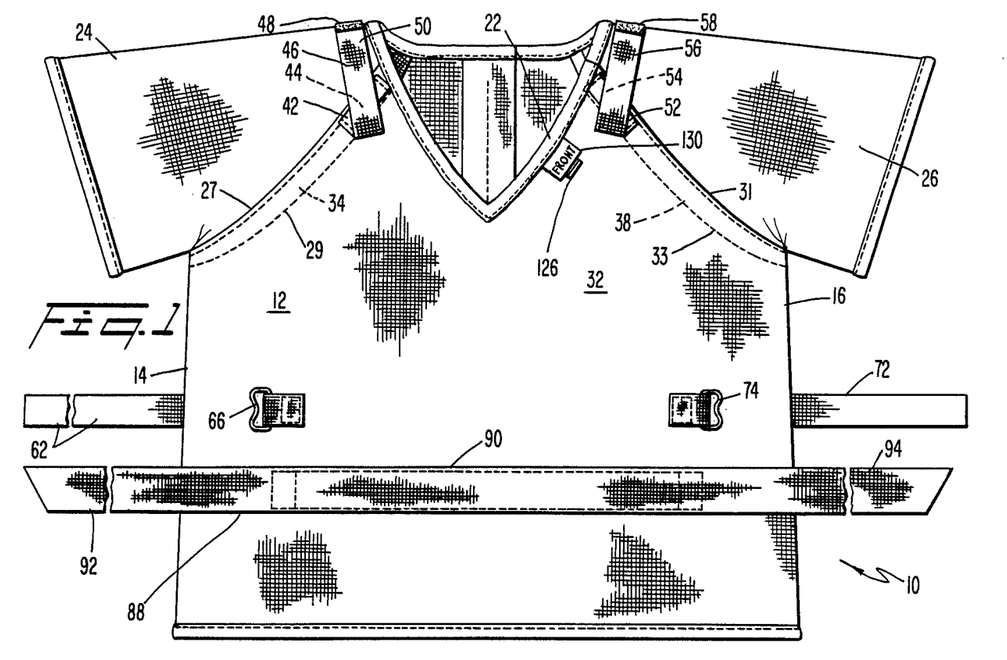
FIG. 1 is a front elevational view of a first embodiment of the novel restraint jacket.

Referring now to FIG. 1, it will there be seen that a first embodiment that illustrates the teachings and suggestions of this invention is denoted as a whole by the reference numeral 10.

Restraint jacket 10 has a front part 12, (FIG. 1), side parts 14, 16 (best shown in FIGS. 8-10) integral thereto, and confronting, slightly overlapping back parts 18, 20, (FIG. 2) integral to said side parts 14, 16, respectively.

A neck opening 22 of the "V" neck type and short sleeve members 24, 26 complete the basic structure of the jacket. The jacket is put on and taken off by separating the confronting back flaps 18, 20 and inserting or withdrawing the patient's hands and arms through sleeves 24, 26, as perhaps best understood in connection with FIG. 4. Thus, the jacket is very easy to put on and take off.

Flaps 28 and 32 and their respective closure means are perhaps the most important features of this invention; they enable facile exposure of the patient's subclavian area.

Each flap 28, 32 is closed by two separate and distinct sets of closure means to defeat facile opening thereof by the patient while presenting no appreciable obstacle to the health care professional caring for said patient.

Each flap is bounded on its inner side by "V" neck 22. Flap 28 is bounded on its outer side by edge 27 of the material from which jacket 10 is made. The material contiguous to edge 27 overlies the jacket material contiguous to sleeve lower edge 29. Flap 32 is bounded on its outer side by edge 31 which overlies sleeve lower edge 33. Thus, the outer edge of each flap overlies the lower edge of its associated sleeve member.

The first closure means for flap 28 includes a first elongate Velcro strip 34 that is fixedly secured to and underlies the part of jacket front 12 adjacent overlying edge 27 and a second Velcro strip, not specifically shown, that is fixedly secured to and overlies the part of jacket front 12 adjacent underlying sleeve edge 29, said second Velcro strip being disposed in underlying registration with strip 34.

Similarly, the first closure means for flap 32 includes a first elongate Velcro strip 38 that is fixedly secured to and underlies the part of jacket front 12 adjacent edge 31 and a second elongate Velcro strip 40 (FIG. 8) that is fixedly secured to and which overlies the part of the jacket adjacent edge 33.

The second closure means for flap 28 is one of the loop lock type. A first strip of material 42 is disposed in overlying relation to front part 12 and is fixedly secured at its opposite ends thereto adjacent "V" neck opening 22; it is aligned with the first closure means as shown. Importantly, the medial part 44 of strip of loop 42 is not attached to jacket front part 12.

A second strip of flexible material 46 is the locking strip of the loop lock and has a first proximal end 48 fixedly secured to the top of sleeve 24 and said locking strip 46 further has a free distal end 50. A Velcro pad having hooks is secured to and overlies secured end 48 of locking strip 46; an elongate Velcro pad having loops overlies the balance of locking strip 46. The second closure means supplements the first closure means as aforesaid and is employed by passing free end 50 of locking strip 46 under medial part 44 of loop member 42 and thereafter reversely bending strip 46 and placing the Velcro pad having loops into mating engagement with the Velcro pad having hooks. The velcro pads provide a large mating surface to increase the strength of the hold.

Similarly, the second closure means for flap 32 is also of the loop lock type. It includes loop member 52 secured to jacket front part 12 at its opposite ends and unsecured medial part 54. Flexible locking strip 56 having secured end 58 covered with a Velcro pad having hooks, and having a Velcro pad having loops along the remainder thereof is used in the same manner as locking strip 46 to secure the second flap 32 at its top end.

Figure 2:
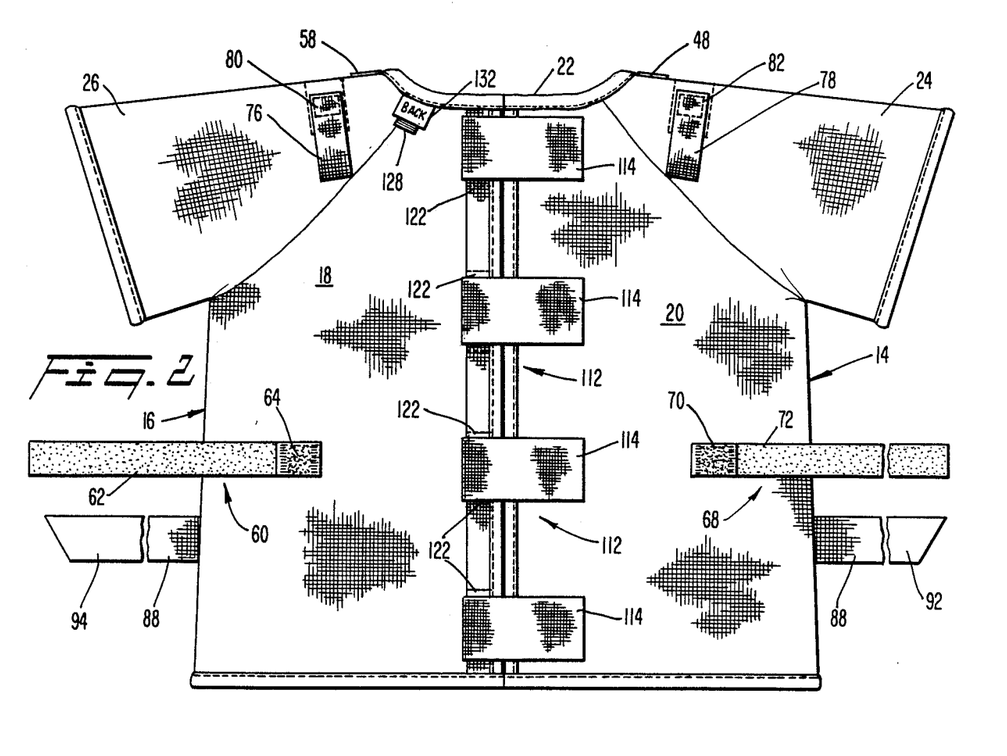
FIG. 2 is a back elevational view of the jacket of FIG. 1.
Figure 8:
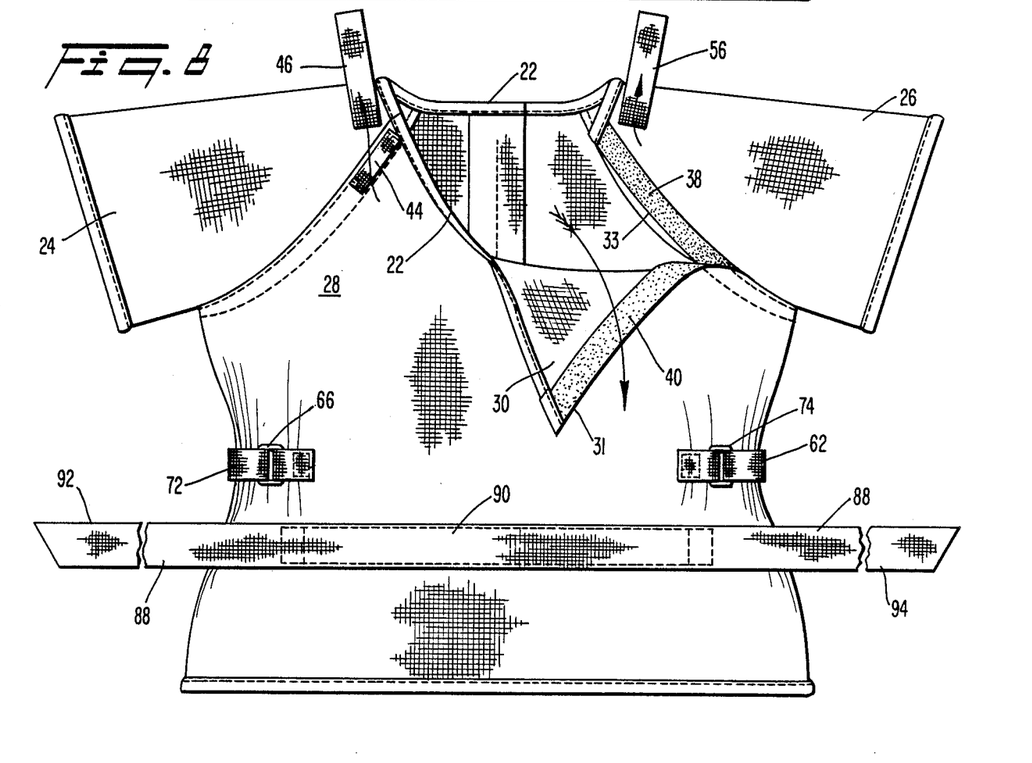
FIG. 8 is a front elevational view, showing one of the flaps folded forwardly.

Loop lock means of substantially the same construction are provided on sides 14 and 16, respectively, of jacket 10; when tightened, they serve to remove play from jacket 10, i.e., they cause the front, sides and back of the jacket to tightly overlie the upper body of the patient so that no rubbing occurs as depicted in FIGS. 7 and 8. As shown in FIG. 2, the free part 62 of locking strip 60 is covered with Velcro loops and the secured end 64 thereof is covered with Velcro hooks. Free part 62 is passed through loop member 66 (FIG. 1) and reversely folded so that the loops thereon are engaged by the hooks of pad 64. Similarly, the loop lock means associated with side 14 of the jacket includes locking strip 68 including Velcro pad 70 with hooks fixedly secured to back jacket flap 20 and wherein the balance 72 of said strip is covered with Velcro loops. Free part 72 is passed through loop 74 (FIG. 1) and reversely folded to complete the loop lock.

Shoulder loops 76 and 78 are laterally spaced with respect to one another as shown in FIG. 2 and are spaced rearwardly of the top of the shoulder. It should be understood that the opposite ends of each shoulder loop 76, 78 is fixedly secured as by sewing to jacket 10 as at 80, 82.

A pair of tether straps, 84, 86 (FIG. 10) have a first end fixedly secured to the upper cross bar of a wheelchair or the upper cross bar of a bed frame and have a second end releasably secured to an associated shoulder loop 76, 78 to prevent the patient from sliding downwardly from a seated position.

Figure 9:
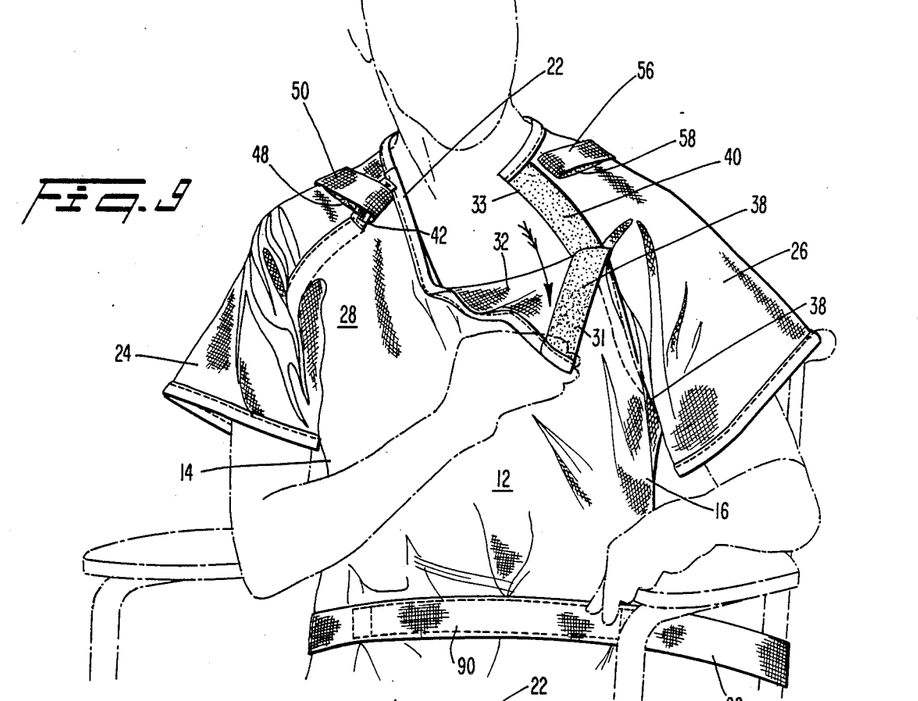
FIG. 9 is a perspective view of the jacket being worn and with one of the flaps being folded forwardly by an alert and limber model.
Figure 10:
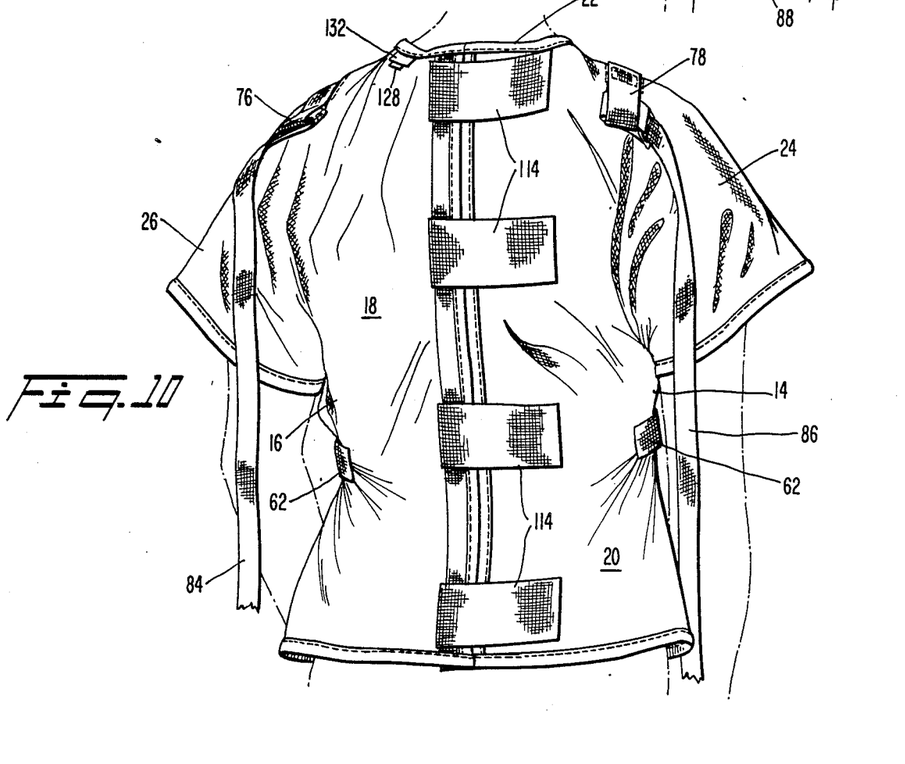
FIG. 10 is a perspective view showing the back of the jacket when worn.

Transversely disposed, elongate strap member 88 has a medial part 90 fixedly secured to the stomach-overlying part of jacket front 12 and opposite free ends 92, 94; the free ends may be tied to one another, as suggested in FIG. 9, around a wheelchair or a bed in accordance with the circumstances in order to restrain the patient.

Back flaps 18, 20 of jacket 10 are also provided with dual closure means, similar to the dual closure means of flaps 28, 32. The primary difference is that the primary closure means is non-continuous and that a plurality of vertically spaced loop lock members provide the second closure means.

Figure 3:
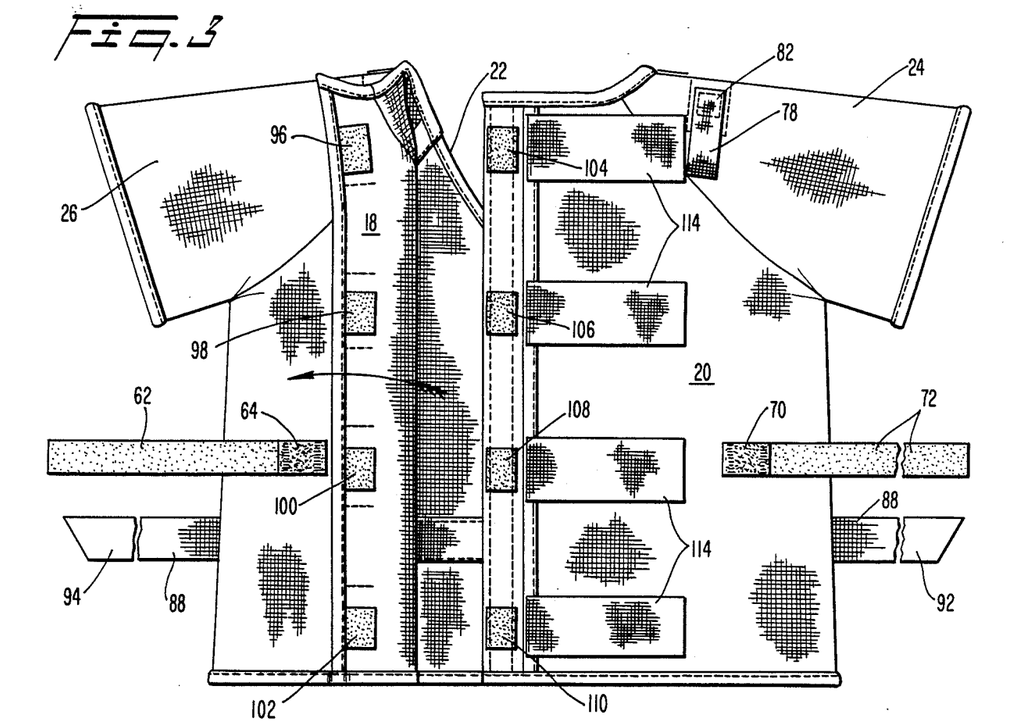
FIG. 3 is a back elevational view, showing the jacket being opened from the back.
Figure 4:
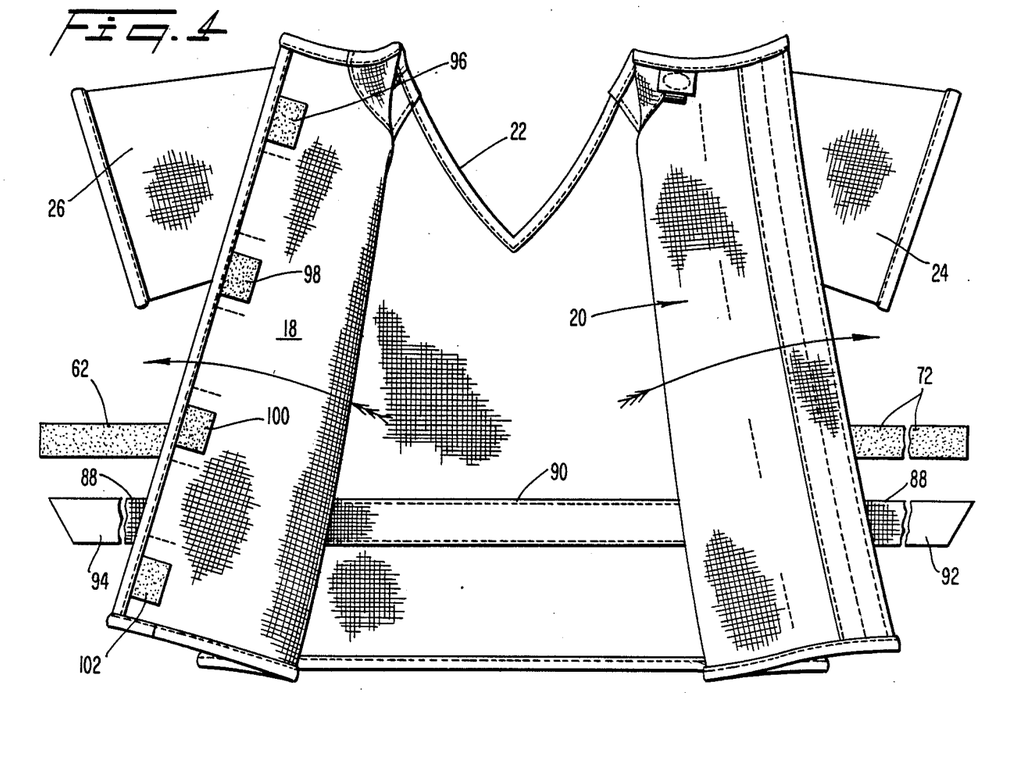
FIG. 4 is a back elevational view, showing the continued opening of the jacket from the back.

More particularly, the first closure means for releasably securing the confronting and slightly overlapping edges of back flaps 18, 20 together includes first, second, third and fourth Velcro pads 96, 98, 100, 102 that underlie flap 18 and corresponding Velcro pads 104, 106, 108, 110 that overlie flap 20 along the edge thereof as shown in FIGS. 3 and 4.

Figure 5:
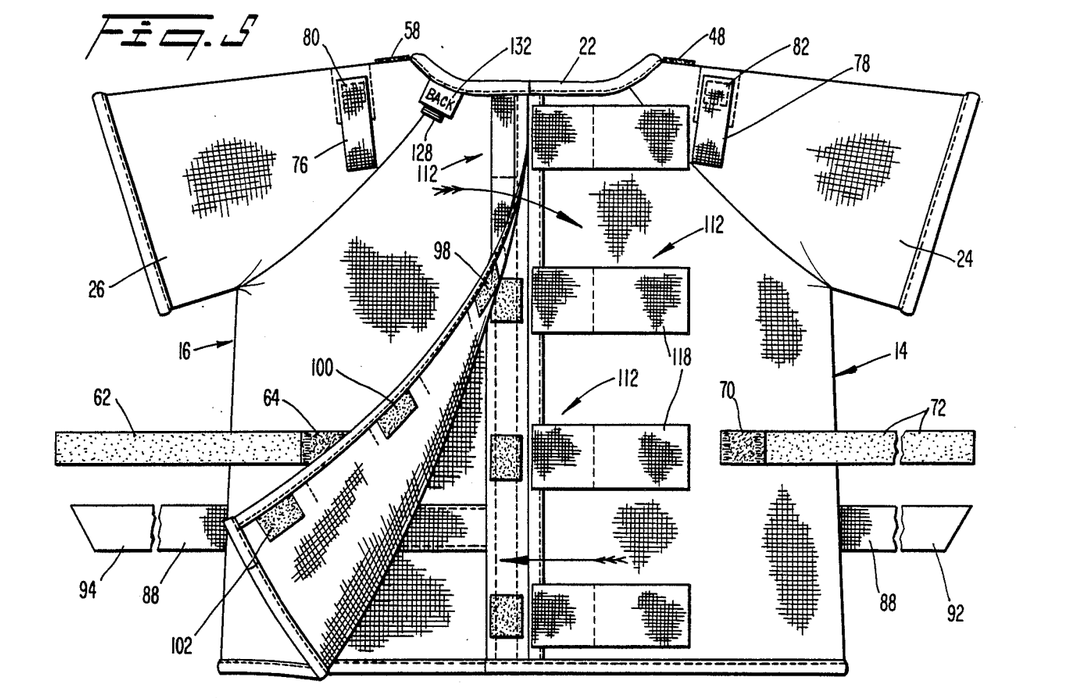
FIG. 5 is a back elevational view, showing a step in closing the back of the jacket.
Figure 6:
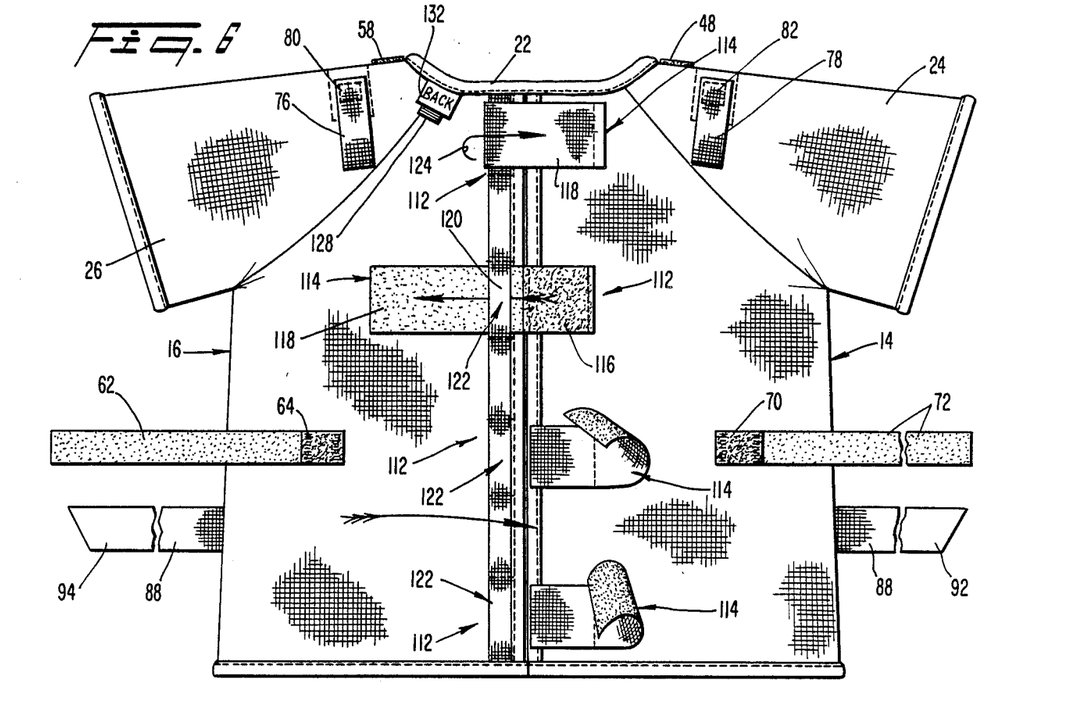
FIG. 6 is a back elevational view, showing another step in the closing of the back of the jacket.

The second closure means includes a plurality of vertically spaced loop lock assemblies, collectively denoted 112 in FIGS. 5 and 6. The structure of each loop lock assembly is substantially the same as the earlier-described loop lock assemblies. Locking strip 114 in FIG. 6 having hooks 116 at its secured end and loops 118 at its free end is shown extended under medial part 120 of loop member 122. Arrow 124 indicates that the distal free end 118 of the top locking strip 114 has been reversely folded to form the loop lock.

As shown in FIGS. 1 and 2 first color coded tab member 126 is secured to the front of the jacket adjacent neck opening 22 and a second color coded tab member 120 is secured to the back of the jacket adjacent the neck opening. A green-in-collar tab could represent a "small" size jacket; yellow might indicate a "medium" size and a third color might indicate a "large" size, for example.

A white tab 130 marked "FRONT" in black letters partially overlies tab 126 as shown to assist the health care professional in the robing process; a white tab 132 marked "BACK" in black letters partially overlies tab 128 as shown for the same reason.

Figure 11:
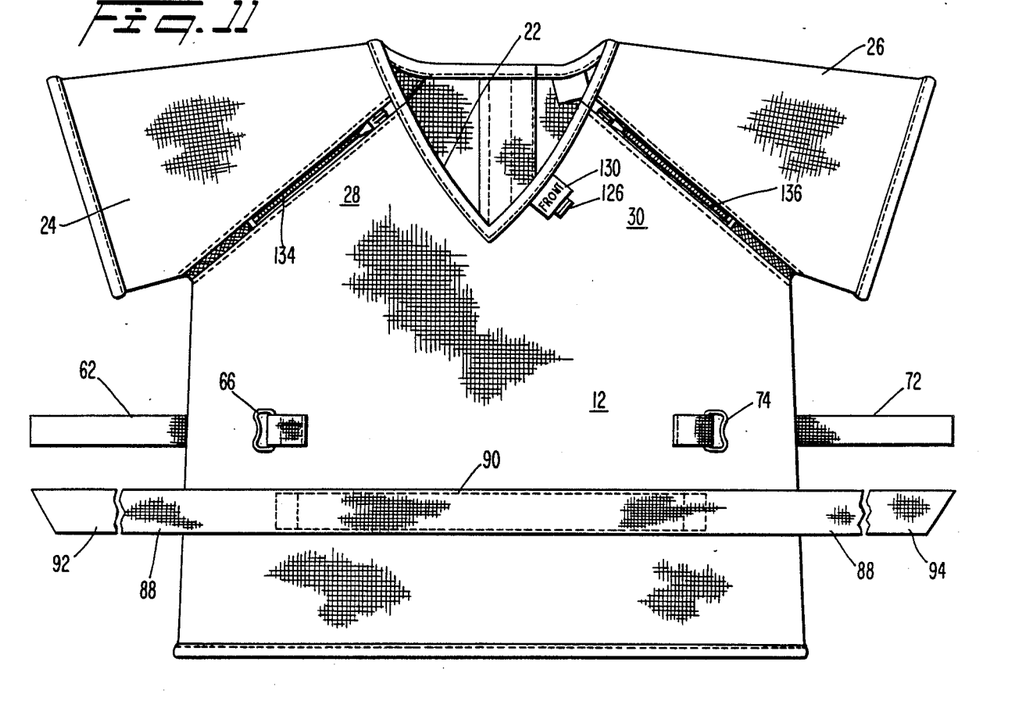
FIG. 11 is a front elevational view of a second embodiment of this invention.
Figure 12:
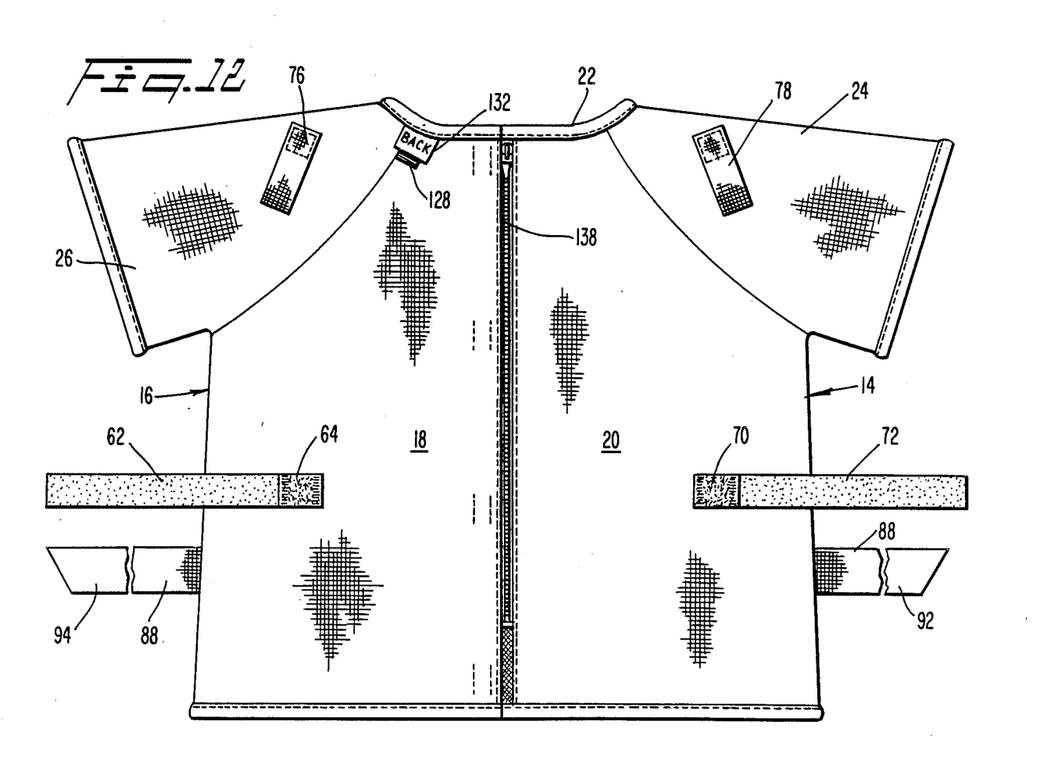
FIG. 12 is a back elevational view of the second embodiment.
Figure 13:
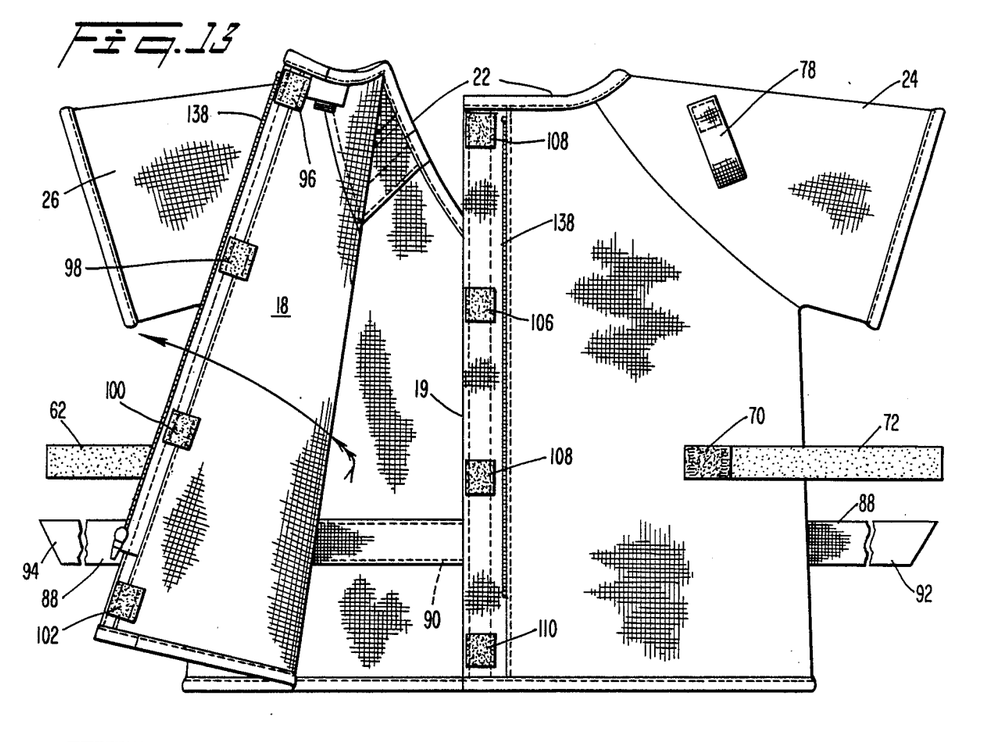
FIG. 13 is a back elevational view showing the opening of the back of the second embodiment.
Figure 14:
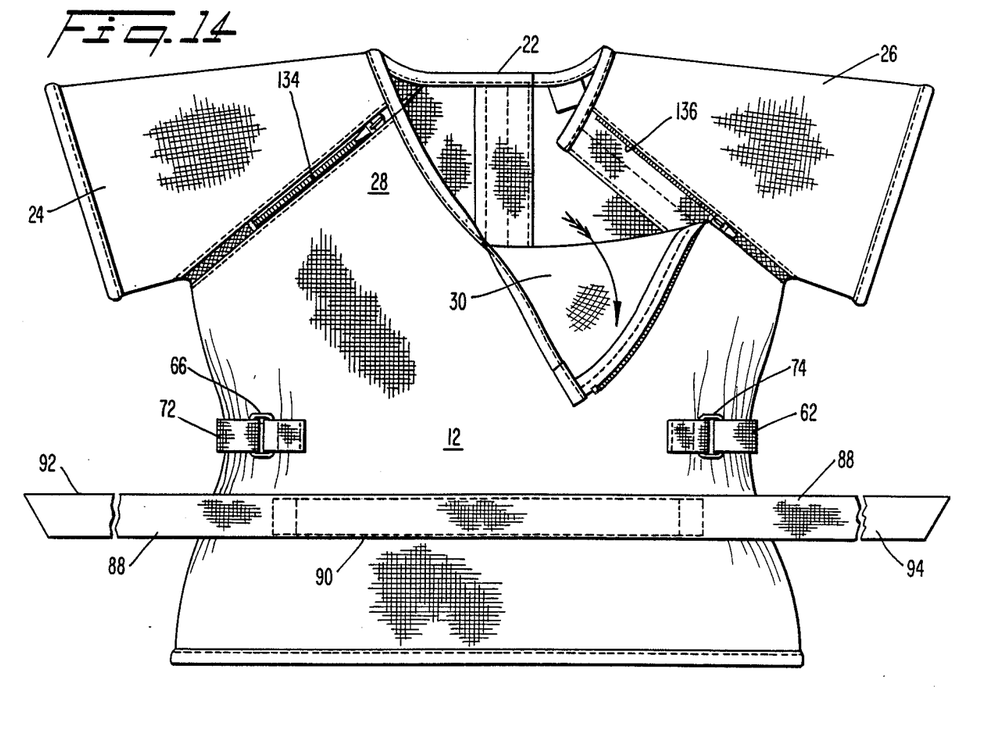
FIG. 14 is a front elevational view of the second embodiment, showing one of the flaps folded forwardly.

FIGS. 11 and 12 show an alternative embodiment including zipper means 134 and 136 o the front of the jacket in lieu of Velcro strips and a zipper 138 for closing the back of the jacket. As shown in FIG. 13, Velcro pads 96, 98, 100, 102 on the underside of flap 18 mate with pads 104, 106, 108, 110 that overlie flap 20 adjacent to edge 19 thereof, thereby providing a backup closure means.

Figure 15:
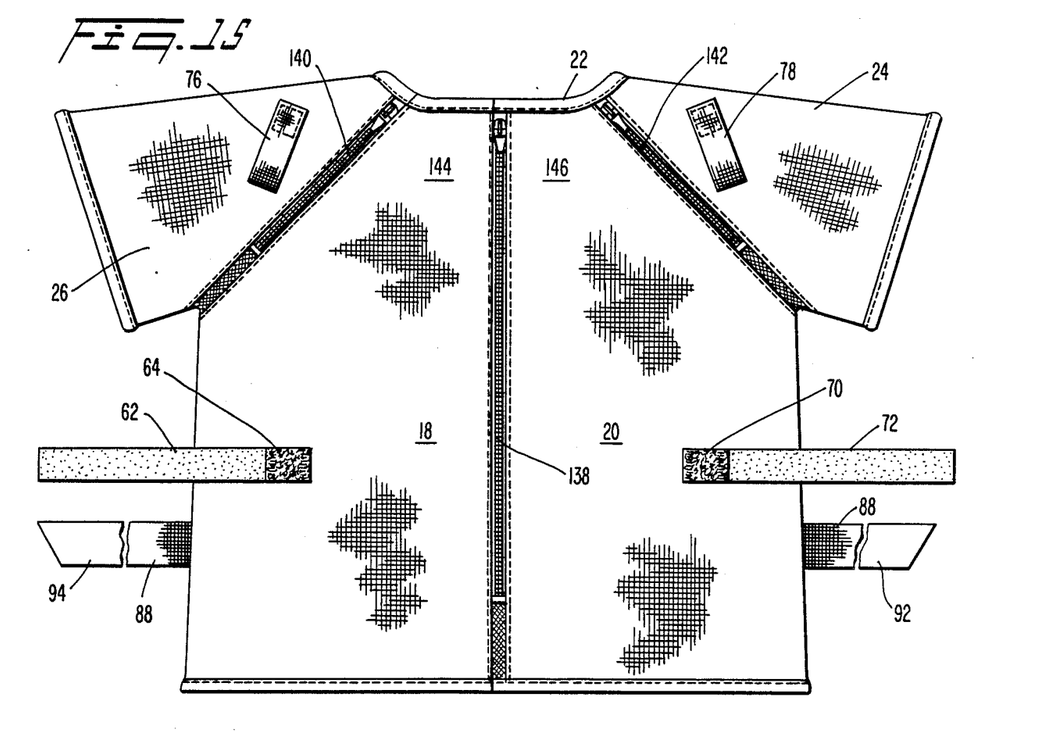
FIG. 15 is a back elevational view of a third embodiment of the invention.
Figure 16:
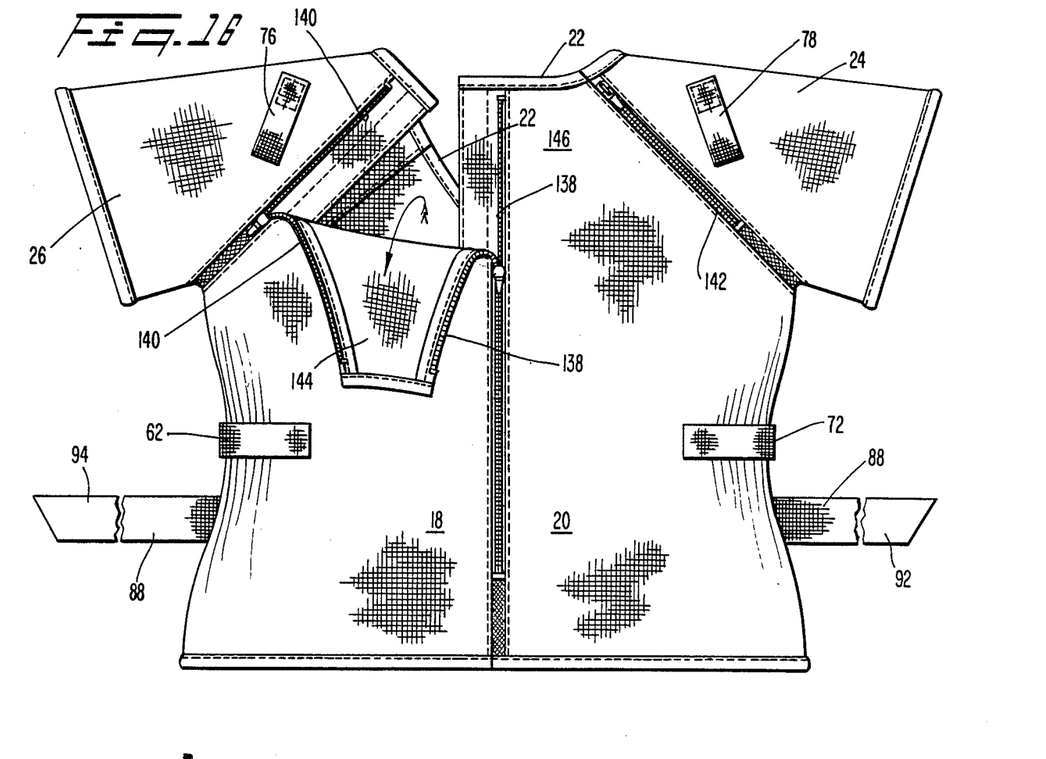
FIG. 16 is a back elevational view of the third embodiment, showing one of the rear flaps being folded forwardly.

FIGS. 15 and 16 show the back of still another embodiment. Zippers 140 and 142 enable back flaps 144, 146 to be opened as depicted in FIG. 16. In effect, the back of the jacket, in this embodiment, is provided with foldable flaps just like the front of the jacket. However, due to the provision of zipper 138, each back flap can be folded downwardly even further than the front flaps 28, 32. Zippers 140, 142 define the outer edges of flaps 144, !46, respectively. The outer edge follows the lower edge of sleeves 24, 26, but, like the Velcro fasteners of the first embodiment, does not extend all the way to the armpit of the jacket as shown.

The present inventive garment was introduced to the marketplace a few months prior to the filing date of this disclosure and met with an immediate and outstanding commercial success, even though no special marketing techniques were employed. The jacket has clearly filled a long standing need for a restraint jacket that is easy for a health care professional to put on a patient. The dual closure means for the flaps that provide access to the subclavian area and the dual closure means for the back of the jacket, while easy for the care provider to handle, resist facile removal of the jacket by the patient, which is highly desirable.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:
1. A restraint jacket, comprising:
a front part that overlie a patient's chest and stomach;
left and right side parts, integral with said front part, that overlie the patient's left and right sides, respectively;
left and right confronting and slightly overlapping back parts, integral with said left and right side parts, respectively, that overlie the patient's back;
a first back part having an edge that overlies and edge of a second back part;
a neck opening;

left and right sleeve members;

a first flap means being formed in said front part;

first closure means for releasably closing said first flap means;

second closure means for releasably closing said first flap means;

a second flap means being formed in said front part in laterally spaced relation to said first flap means;

third closure means for releasably closing said second flap means;

fourth closure means for releasably closing said second flap means;

whereby the provision of said first and second closure means substantially defeats facile opening of said first flap means by the patient;

whereby the provision of said third and fourth closure means substantially defeats facile opening of said second flap means by the patient;

whereby a first subclavian area of the patient's chest is exposed by releasing said first and second closure means and folding forward said first flap means; and whereby a second subclavian area of the patient's chest is exposed by releasing said third and fourth closure means and folding forward said second flap means.

2. The jacket of claim 1, wherein said neck opening is a "V"-shaped neck opening.

3. The jacket of claim 2, wherein opposite peripheral borders of said neck opening form the inner edges of said first and second flap means.

4. The jacket of claim 3, wherein the outer edge of each flap means extends from substantially the top of said neck opening along a substantially linear path of travel toward an armpit area of said jacket.

5. The jacket of claim 4, wherein each outer edge of each of said flap means has a lowermost point remote from said armpit area.

6. The jacket of claim 5, wherein each flap means outer edge overlies a lower peripheral edge of its associated sleeve member.

7. The jacket of claim 6, wherein said first closure means for releasably closing said first and second flap means includes a releasable fastening means secured in overlying relation adjacent said lower peripheral edge of each sleeve member.

8. The jacket of claim 7, wherein said first closure means for releasably closing said first and second flap means includes a releasable fastening means secured in underlying relation to the outer edge of each flap means.

9. The jacket of claim 8, wherein the releasable fastening means secured to said lower edges of said sleeve members and the outer edges of said flap means are mating, complementally formed strips of hook and loop fasteners.

10. The jacket of claim 9, wherein the second closure means includes a loop lock means disposed adjacent the top of each of said outer edges of said first and second flap means.

11. The jacket of claim 10, wherein each of said loop lock means includes a loop member having opposite ends fixedly secured to its associated flap means adjacent the outer edge thereof in overlying relation thereto, each of said loop means having an unsecured medial part disposed in overlying relation to said flap means adjacent its associated outer edge.

12. The jacket of claim 11, wherein each of said loop lock means further includes an elongate flexible locking strip, each of said locking strips having a first end secured in overlying relation to its associated sleeve member, adjacent an inner end of each sleeve member, and each of said locking strips having a longitudinal extent sufficient to pass under its associated loop member and to reversely bend back so that a distal free end thereof overlies said fixedly secured end, said fixedly secured end and said distal free end being covered with mating hook and loop fastening means.

13. The jacket of claim 12, further comprising first and second closure means for releasably securing together said left and right confronting and slightly overlapping back parts.

14. The jacket of claim 13, wherein said first closure means for releasably securing said back parts together includes at least one hook and loop fastening means, a first part of which is secured to an underlying surface of an overlying edge of a first back flap and a second part of which is secured to an overlying surface of an underlying edge of a second back flap.

15. The jacket of claim 14, wherein said second closure means for releasably securing said back parts together includes a plurality of vertically spaced loop lock means.

16. The jacket of claim 14, wherein said second closure means is a zipper member.

17. The jacket of claim 1, further comprising a left and right loop lock means secured to said left and right side parts.

18. The jacket of claim 17, further comprising an elongate strap member having a medial part fixedly secured to the stomach-overlying part of said jacket and having elongate opposite ends permitting tying thereof around a stationary object.

19. The jacket of claim 16, further comprising a third and fourth flap means formed in said back parts of said jacket.

20. The jacket of claim 19, wherein said third and fourth flap means have respective inner edges bounded by said second closure means.

21. The jacket of claim 20, wherein outer edges of said third and fourth flap means are disposed in confronting relation to lower edges of their associated sleeve members.

22. The jacket of claim 21, wherein said confronting edges of said sleeve members and said back third and fourth flaps are releasably secured to one another by zipper means.

23. A restraint jacket, comprising:

a front part that overlies a patient's chest and stomach;

left and right side parts, integral to said front part, that overlie the patient's left and right sides, respectively;

left and right confronting ad slightly overlapping back parts, integral to said left and right side parts, respectively, that overlie the paient's back;

a first back part having an edge that overlies an edge of a second back part;

a neck opening;

left and right sleeve members;

a first closure means for releaseably securing together said left and right back parts;

a first flap means being formed i said first back part on a first side of said first closure means;

said first closure means forming an inner peripheral boundary of said first flap means;
a second closure means forming an outer peripheral boundary of said first flap means;
said second closure means extending substantially from a back part of said neck opening toward a first armpit area of said jacket;
a second back part having an edge that underlies an edge of a first back part;
a second flap means being formed in said second back part on a second side of said first closure means;
said first closure means forming an inner peripheral boundary of said second flap means;
a third closure means forming an outer peripheral boundary of said second flap means;
said third closure means extending substantially from a back par of said neck opening toward a second armpit area of said jacket;
whereby opening said first and second closure means permits folding of said first flap means to thereby expose the upper part of a patient's back on a first side of said first closure means;
whereby opening in said first and third closure means permits folding of said second flap means to thereby expose the upper part of a patient's back on a second side of said first closure means.

* * * * *